United States Patent [19]

Perregaard et al.

[11] Patent Number: 5,684,012
[45] Date of Patent: Nov. 4, 1997

[54] DIMERIC PIPERIDINE, TETRAHYDROPYRIDINE AND PIPERAZINE DERIVATIVES

[75] Inventors: Jens Perregaard, Jægerspris; John W. Stenberg, Copenhagen-Valby; Ejner K. Moltzen, Frederiksberg, all of Denmark

[73] Assignee: H. Lundbeck A/S, Copenhagen-Valby, Denmark

[21] Appl. No.: 486,740

[22] Filed: Jun. 7, 1995

Related U.S. Application Data

[62] Division of Ser. No. 354,280, filed as PCT/DK93/00198, Jun. 9, 1993, published as WO93/25527, Dec. 23, 1993.

Foreign Application Priority Data

Jun. 12, 1992 [DK] Denmark ................ 0786/92

[51] Int. Cl.[6] ................ C07D 401/12; C07D 401/06; C07D 403/12; C07D 403/06
[52] U.S. Cl. ................ 514/278; 546/18
[58] Field of Search ................ 546/18; 514/278

[56] References Cited

U.S. PATENT DOCUMENTS

| | | | |
|---|---|---|---|
| 2,891,066 | 6/1959 | Parcell | 260/294.3 |
| 3,408,356 | 10/1968 | Horovitz | 260/294.3 |
| 3,476,760 | 11/1969 | Kaiser et al. | 546/201 |
| 3,558,637 | 1/1971 | Kaiser et al. | 546/201 |
| 3,686,186 | 8/1972 | Houlihan et al. | 260/293.58 |
| 3,745,165 | 7/1973 | Houlihan et al. | 260/293.77 |
| 3,962,259 | 6/1976 | Bauer et al. | 260/293.58 |
| 3,980,658 | 9/1976 | Possanza et al. | 260/293.61 |
| 3,985,889 | 10/1976 | Bauer et al. | 424/267 |
| 3,996,211 | 12/1976 | Lassen | 260/240 |
| 4,038,395 | 7/1977 | Lassen | 424/250 |
| 4,208,417 | 6/1980 | Uzan et al. | 424/267 |
| 4,420,485 | 12/1983 | Davis et al. | 424/267 |
| 4,443,448 | 4/1984 | Bøgesø | 424/250 |
| 4,452,802 | 6/1984 | Kosley, Jr. et al. | 424/267 |
| 4,525,360 | 6/1985 | Perregaard | 514/277 |
| 4,530,932 | 7/1985 | Clemence et al. | 514/318 |
| 4,670,447 | 6/1987 | Strupczewski | 514/322 |
| 4,684,650 | 8/1987 | Bogeso | 514/252 |
| 4,772,612 | 9/1988 | Goldmann et al. | 514/302 |
| 4,831,254 | 5/1989 | Lowe, III et al. | 514/254 |
| 4,853,470 | 8/1989 | Strupczewski | 546/199 |
| 4,873,344 | 10/1989 | Bogeso et al. | 541/77 |
| 4,943,590 | 7/1990 | Boegesoe et al. | 514/469 |
| 4,946,863 | 8/1990 | Boegesoe et al. | 514/447 |

FOREIGN PATENT DOCUMENTS

| | | | |
|---|---|---|---|
| 247250 | 9/1962 | Australia . | |
| 0 224 919 A2 | 6/1987 | European Pat. Off. | C07D 417/14 |
| 0 259 782 B1 | 3/1988 | European Pat. Off. | C07C 217/78 |
| 0 281 309 B1 | 9/1988 | European Pat. Off. | C07D 263/58 |
| 0 376 607 B1 | 7/1990 | European Pat. Off. | C07D 209/14 |
| 0 399 982 A1 | 11/1990 | European Pat. Off. | C07C 211/42 |
| 0 414 289 B1 | 2/1991 | European Pat. Off. | C07D 221/20 |
| 0 431 943 A2 | 6/1991 | European Pat. Off. | C07D 491/10 |
| 0 445 974 A2 | 9/1991 | European Pat. Off. | A61K 31/445 |
| 1 335 831 | 10/1962 | France . | |
| 2 391 211 | 4/1976 | France | C07D 405/14 |
| 55-143980 | 11/1989 | Japan | C07D 311/96 |
| 1 438 094 | 6/1976 | United Kingdom | C07D 401/04 |
| WO90/14067 | 11/1990 | WIPO . | |
| WO91/03243 | 3/1991 | WIPO | A61K 31/445 |
| WO91/09594 | 7/1991 | WIPO | A61K 31/085 |
| WO92/00070 | 1/1992 | WIPO | A61K 31/445 |
| WO92/10192 | 6/1992 | WIPO | A61K 31/495 |

OTHER PUBLICATIONS

Bally et al. (1887) *Chem. Ber.*, vol. 20, p. 2590.
Barry et al. (1987), "Withdrawal Syndrome Following Subchronic Treatment with Anxiolytic Agents", *Pharmac. Biochem. Behav.*, vol. 27, pp. 239–245.

(List continued on next page.)

*Primary Examiner*—Mark L. Berch
*Assistant Examiner*—Bruck Kifle
*Attorney, Agent, or Firm*—Darby & Darby

[57] ABSTRACT

This subject invention relates to dimeric 4-phenylpiperidine, 4-phenyl-1,2,3,6-tetrahydropyridine, or 4-phenylpiperazine compounds or dimeric spirocyclic piperidine compounds having general formula (I),

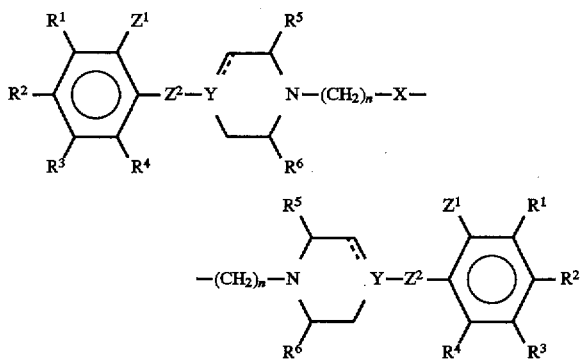

wherein n is 1–5; $R^1$ to $R^4$ are substituents; $R^5$ and $R^6$ each hydrogen or alkyl or form together an ethylene or propylene bridge; X is O, S, SO, $SO_2$, CO or $(CH_2)_m$, being 0 or 1, X is $NR^7$, $R^7$ being H, alkyl, cycloalkyl, cycloalkylalkyl, phenyl, or phenylalkyl, or X is $CR^8 R^9$, wherein $R^8$ and $R^9$ are selected from hydroxy and the substituents defined under $R^7$; and (i) $Z^1$ is a substituent and $Z^2$ is $(CH_2)_p$ wherein p is 0; and Y is N, C or CH; (ii) $Z^1$ and Y are linked together via a single bond, thereby forming a spirocyclic junction; in which case Y is C; $Z^1$ is O, S, $(CH_2)_q$, q being 1, 2 or 3, or $Z^1$ is $CH_2O$, $CH_2S$, $CH_2CH_2O$, $CH_2CH_2S$, $CH=CH$, $CH=CHCH_2$, $CH_2OCH_2$, $CH_2SCH_2$, $CH=CH-O$, or $CH=CH-S$; and $Z^2$ is O, S or $(CH_2)_p$, p being 0 or 1; are potent sigma receptor ligands thus being useful as drugs for the treatment of anxiety, psychosis, epilepsy, convulsion, movement disorders, motor disturbances, amnesia, cerebrovascular diseases, senile demential of the Alzheimer type or Parkinson's disease.

14 Claims, No Drawings

OTHER PUBLICATIONS

Bøgesø, K. P. et al. (1985) "3–Phenyl–1–indanamines. Potential Antidepressant Activity and Potent Inhibition of Dopamine, Norepinephrine, and Serotonin Uptake", *J. Med. Chem.*, vol. 28, pp. 1817–1828.

Bøgesø, K. P. (1983), "Neuroleptic Activity and Dopamine–Uptake Inhibition in 1–Piperazino–3–phenylindans", *J. Med. Chem.*, vol. 26, pp. 935–947.

Hyttel, J. et al. (1985), "Neurochemical Profile of Lu 19–005, a Potent Inhibitor of Uptake of Dopamine, Noradrenaline, and Serotonin", *J. Neurochem.*, vol. 44, pp. 1615–1622.

Allen, R. C. et al. (1978), "Synthesis of Spiro[isobenzofuran–1(3), 4'–piperidines] as Potential Central Nervous System Agents. 4. Central Nervous System Depressants", *J. Med. Chem.*, vol. 21, No. 11, pp. 1149–1154.

Perregaard et al. (1992), "Noncataleptogenic, Centrally Acting Dopamine D–2 and Serotonin 5–$HT_2$ Antagonists within a Series of 3–Substituted 1–(4–Flurophenyl)–1H–Indoles", *J. Med. Chem.*, vol. 35, pp. 1092–1101.

Martin et al. (1989), "Activity of Aromatic Substituted Phenylpiperazines Lacking Affinity for Dopamine Binding Sites in a Preclinical Test of Antipsychotic Efficacy", *J. Med. Chem.*, vol. 32, pp. 1052–1056.

Marxer et al. (1975), "Spiro Piperidines. I. Synthesis of Spiro[isobenzofuran–1(3H), 4'–Piperidines] and Spiro [isobenzofuran–1(3H,3'–piperidines]", *J. Org. Chem.*, vol. 40, No. 10, pp. 1427–1433.

McElvain, S. M. et al. (1950), "Piperidine Derivatives. XXIII. Certain Halogenated 1–Methyl–4–Phenylpiperidines and Related Compounds", *J. Amer. Chem. Soc.*, vol. 72, pp. 3134–3138.

McMillen, B. A. et al. (1988), "N–Alkyl–Substituted Aryl–Piperazine Drugs: Relationship Between Affinity for Serotonin Receptors and Inhibition of Aggression", *Drug Develop. Res.*, vol. 12, pp. 53–62.

Rao, T. S. et al. (1990), "Inhibition of Climbing and Mossy Fiber, and Basket and Stellate Cell Inputs to Mouse Cerebellar Purkinje Cells by Novel Anti–Ischemic Agents, Ifenprodil and BMY–14802", *Life Sciences*, vol. 47, pp. PL–1–PL–5.

Sanchez et al. (1991), "Neurochemical and In Vivo Pharmacological Profile of Sertindole, a Limbic–Selective Neuroleptic Compound", *Drug Deve. Res.*, vol. 22, pp. 239–250.

Schweizer, E. et al. (1986), "Failure of Buspirone to Manage Benzodiazepine Withdrawal", *Am. J. Psychiat.*, vol. 143, No. 12, pp. 1590–1592.

Skarsfeldt, T. et al. (1990), "Sertindole, A New Neuroleptic with Extreme Selectivity on A10 Versus A9 Dopamine Neurones in the Rat", *Eur. J. Pharmacol.*, vol. 182, pp. 613–614.

Yamato, M. et al. (1981), "Synthesis and Structure–Activity Relationship of Spiro[isochromanpiperidine] Analogs for Inhibition of Histamine Release", *Chem. Pharm. Bull.*, vol. 29, No. 12, pp. 3494–3498.

Yamato, M. et al. (1981), "Synthesis and Structure–Activity Relationship of Spiro[isochromanpiperidine] Analogues for Inhibition of Histamine Release", *J. Med. Chem.*, vol. 24, pp. 194–198.

Chambers, M. S. et al. (1992), "Spiropiperidines as High–Affinity, Selective α Ligands", *J. Med. Chem.*, vol. 35, pp. 2033–2039.

Rao, Tadimeti S. et al. (1990), "BMY–14802 Antagonizes Harmaline–and D–Serine–Induced Increases in Mouse Cerebellar Cyclic GMP: Neuorochemical Evidence of a σ Receptor–Mediated Functional Modulation of Responses Mediated by the N–Methyl–D–aspartate Receptor Complex In Vivo", *Molecular Pharmacology*, vol. 37, pp. 978–982.

Walker, J. M. et al. (1990) *Pharmacological Reviews*, vol. 42, p. 355.

Earley et al. (1991) *Brain Research*, vol. 546, pp. 281–286.

Hyttel, J. (1987), "Age Related Decrease in the Density of Dopamine $D_1$ and $D_2$ Receptors in Corpus Striatum of Rats", *Pharmacology and Toxicology*, vol. 61, pp. 126–129.

Hyttel, J. et al. (1988), "Neurochemical Profile In Vitro of Irindalone: A 5–$HT_2$–Receptor Antagonist", *Drug. Dev. Res.*, vol. 15, pp. 389–404.

Junien et al. (1991), "JO1784, A Novel α Ligand, Potentiates [$^3$H]Acetylcholine Release from Rat Hippocampal Slices", *Eur. J. Pharm.*, vol. 200, pp. 343–345.

Matsuno et al. (1992), "Increase of Extracellular Acetylcholine Level in Rat Frontal Cortex Induced by (+)N–allylnormetazocine as Measured by Brain Microdialysis", *Brain Research*, vol. 545, pp. 315–319.

Parham et al. (1976), *J. Org. Chem.*, vol. 41, p. 2628.

Skarsfeldt, T. et al. (1986), "The St 587–Induced Flexor Reflex in Pithed Rats: A Model to Evaluate Central $α_1$–Receptor Blocking Properties", *Eur. J. Pharmacol.*, vol. 125, pp. 333–340.

Van der Weider, J. et al. (1987), "In Vitro Binding of the Very Potent and Selective D–2 Dopamine Agonist, [$^3$H]N–0437 to Calf Caudate Membranes", *Eur. J. Pharmacol.*, vol. 134, pp. 211–219.

Weber, E. et al., (1986), "1,3–Di(2–[5–$^3$H]tolyl)guanidine: A Selective Ligand that Labels α–type Receptors for Psychotomimetic Opiates and Antipsychotic Drugs", *Proc. Natl. Acad. Sci.*, vol. 83, pp. 8784–8788.

Snyder, S.H. et al. (1989), "Receptor Mechanisms in Antipsychotic Drug Action: Focus on Sigma Receptors," *Neuropsychiatry*, vol. 1, p. 7.

Colpaert, F.C. et al. (1985), *Psychopharmacology*, vol. 86, pp. 303–305.

DIMERIC PIPERIDINE, TETRAHYDROPYRIDINE AND PIPERAZINE DERIVATIVES

This is a division, of application Ser. No. 08/354,280, filed Dec. 12, 1994, which is a continuation of International Application No. DK93/00198, filed Jun. 9, 1993.

The present invention relates to a novel class of dimeric piperidine, 1,2,3,6-tetrahydropyridine and piperazine derivatives in which the nitrogen atoms of the six-membered basic rings are linked together via a spacer chain to form a symmetrical dimeric bis(1-piperidyl), bis(1,2,3,6-tetrahydro-1-pyridyl), or bis(1-piperazinyl) compound. These dimers potently bind to sigma receptors and are therefore useful in the treatment of certain psychic and neurologic disorders. The piperidines, 1,2,3,6-tetrahydropyridines, or piperazines are substituted with 4-phenyl groups or the piperidine derivatives might be spiro-joined in the 4-position to a hetero- or carbocyclic ring system.

Various 4-phenylpiperidine, 4-phenyl-1,2,3,6-tetrahydropyridines, 4-phenylpiperazines, and spirocyclic piperidine derivatives have previously been described:

International Patent Application No WO 91/09594 generically describes a broad class of sigma receptor ligands some of which are 4-phenylpiperidine, —tetrahydropyridine or —piperazine compounds having an optionally substituted "aryl"— or "heteroaryl" -alkyl, -alkenyl, -alkynyl, -alkoxy or -alkoxyalkyl substituent on the ring N-atom. The terms "aryl" and "heteroaryl" are defined by mention of a number of such substituents.

European patent publication No EP 0 414 289 A1 generically discloses a class of 1,2,3,4-tetrahydro-spiro [naphthalene-1,4'-piperidine] and 1,4-dihydro-spiro [naphthalene-1,4'-piperidine] derivatives substituted at the piperidine N-atom with a "hydrocarbon" group alleged to have selective sigma receptor antagonistic activity. The term "hydrocarbor" as defined in said patent covers all possible straight chained, cyclic, heterocyclic, etc. groups. However, only compounds having benzyl, phenethyl, cycloalkylmethyl, furyl— or thienylmethyl or lower alkyl or alkenyl as the "hydrocarbon" substituent at the piperidine nitrogen atom are specifically disclosed. The compounds are stated to displace tritiated di-tolyl guanidine (DTG) from sigma sites with potencies better than 200 nM. As a particularly preferred compound is mentioned 1'-benzyl-1,2,3,4-tetrahydro-spiro[naphthalene-1,4'-piperidine].

European patent publication No EP 0 445 974 A2 generically describes corresponding spiro[indane-1,4'-piperidine] and spiro[benzocycloheptene-5,4'-piperidine] derivatives. Again the compounds are only stated to displace tritiated ditolyl guanidine (DTG) from sigma sites with potencies better than 200 nM EP Application No. EP-A2-0 431 943 relates to a further extremely broad class of spiropiperidine compounds substituted at the piperidine N-atom and claimed to be useful as antiarrhythmics and for impaired cardiac pump function. The said application exemplifies several compounds, the majority of which contain an oxo and/or a sulfonylamino substituent in the spiro cyclic ring system. Of the remainder compounds, the main part has another polar substituent attached to the spiro nucleus and/or they have some polar substituents in the substituent on the piperidine N-atom. No suggestion or indication of effect of the compounds on the sigma receptors is given.

From studies of the biology and function of sigma receptors, evidence has been presented that sigma receptor ligands may be useful in the treatment of psychosis and movement disorders, such as dystonia and tardive dyskinesia, and motor disturbances associated with Huntington's chorea or Tourette's syndrome and in Parkinson's disease (Walker, J. M. et al, *Pharmacological Reviews,* 1990, 42, 355). It has been reported that the known sigma receptor ligand rimcazole clinically shows effects in the treatment of psychosis (Snyder, S. H., Largent, B. L. J. *Neuropsychiatry* 1989, 1,7) and that a group of sigma receptor ligands show antihallucinogenic activity in animal models (International Patent Publication No WO 9103243).

Furthermore, some sigma receptor ligands have been found to be involved in modulation of NMDA receptor mediated events in the brain and to act as antiischemic agents in in vivo tests (Rao, T. S. et al, *Molecular Pharmacology,* 1990, 37, 978 and Rao, T. S. et al, *Life Sciences,* 1990, 47, PL1–PL5). In addition to ischemia they may also be useful in the treatment of other such events. e.g. epilepsy and convulsion.

Also, some sigma receptor ligands have been found to show anti-amnesic effects in an animal model (Early et al., *Brain Research* 1991, 546,281–286).

Sigma ligands have been shown to influence central acetylcholine levels in animal models (Matsuno et al, Brain Research 1992, 575, 315–319; Junien et al, Eur. J. Pharm. 1991, 200, 343–345) and may, therefore, have potential in the treatment of senile dementia, e.g. of the Alzheimer type.

Finally some guanidine derivatives having sigma receptor activity have been disclosed to be useful as anxiolytics (International Patent Publication No. WO 9014067).

Accordingly, agents potently acting on the sigma receptors in the central nervous system may be useful in the therapy of such conditions.

It has now been found that the novel class of dimeric piperidine, 1,2,3,6-tetrahydropyridine and piperazine compounds are potent sigma receptor ligands.

Accordingly the present invention provides the novel dimeric 4-phenylpiperidine, 4-phenyl-1,2,3,6-tetrahydropyridines, or 4-phenylpiperazine derivatives or dimeric spirocyclic piperidine compounds having the general Formula I:

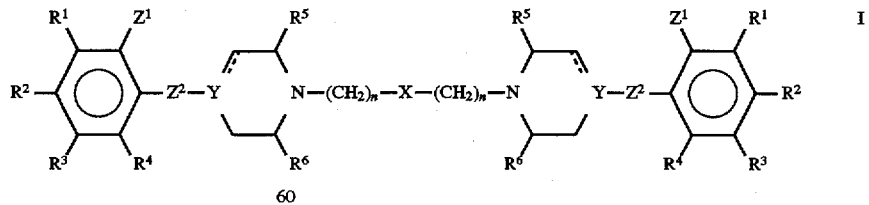

wherein n is 1–5;

$R^1$ to $R^4$ are independently selected from hydrogen, halogen, lower alkyl, lower alkoxy, hydroxy, lower alkylthio, lower alkylsulfonyl, lower alkyl- or dialkylamino, cyano, trifluoromethyl, nitro, trifluoromethylthio or trifluoromethylsulfonyloxy;

$R^5$ and $R^6$ are independently hydrogen, lower alkyl or they may be linked together thereby forming an ethylene or propylene bridge;

X is O, S, SO, $SO_2$, CO or $(CH_2)_m$, m being 0 or 1, X is $NR^7$, $R^7$ being H, lower alkyl, cycloalkyl, cycloalkylalkyl, phenyl, or phenylalkyl, or X is $CR^8R^9$, wherein $R^8$ and $R^9$ are independently selected from the group consisting of hydroxy and the substituents defined under $R^7$, any phenyl group being optionally substituted; and I) $Z^1$ is defined as $R^1$ to $R^4$ and $Z^2$ is $(CH_2)_p$ wherein p is 0; and Y is N, CH or C; and the dotted line indicates an optional bond, i.e. represents a bond when Y is C; or II) $Z^1$ and Y are linked together via a single bond, thereby forming a spirocyclic junction; in which case Y is C and the dotted line represent no bond; and $Z^1$ is O, S, $(CH_2)_q$, q being 1,2, or 3, or $Z^1$ is $CH_2O$, $CH_2S$, $CH_2CH_2O$, $CH_2CH_2S$, CH=CH, CH=$CHCH_2$, $CH_2OCH_2$, $CH_2SCH_2$, CH=CH—O, or CH=CH—S; and $Z^2$ is O, S, or $(CH_2)_p$, p being 0 or 1, with the proviso that $Z^1$ may not be O, S or $(CH_2)_q$, wherein q is 1 when $Z^2$ is $(CH_2)_p$ wherein p is 0;

or an acid addition salt or prodrug thereof.

Some of the compounds of general Formula I may exist as optical isomers thereof; and such optical isomers are also embraced by the invention.

In the definition of general Formula I, halogen means fluoro, chloro, bromo or iodo.

The terms lower alkyl, lower alkoxy, lower alkylthio and lower alkylsulphonyl, etc. designate such branched or unbranched groups having from one to six carbon atoms inclusive. Exemplary of such groups are methyl, ethyl, 1-propyl, 2-propyl, 1-butyl, 2-butyl, 2-methyl-2-propyl, 2-methyl-1-propyl, methoxy, ethoxy, 1-propoxy, 2-propoxy, methylthio, ethylthio, 1-propylthio, 2-propylthio, methylsulphonyl, ethylsulphonyl, or the like. Similarly, lower alkyl- or dialkylamino designate such groups containing lower alkyl as defined above and lower alkenyl is intended to mean an alkenyl group (branched or unbranched) containing from two to six carbon atoms, for example ethenyl, 1-propenyl, 2-propenyl, 3-propenyl, 2-buten-1-yl etc.

The term cycloalkyl designates a carbocycle having 3–8 carbon atoms inclusive.

The optional substituents in the phenyl groups may independently be selected from halogen, lower alkyl, lower alkoxy, hydroxy, lower alkylthio, lower alkylsulfonyl, lower alkyl- or dialkylamino, cyano, trifluoromethyl, or trifluoromethylthio. Each phenyl group may carry one or more substituents.

In the definition of $Z^1$ under II) the groups listed may be oriented in both directions, i.e. for example the group $CH_2O$ may be linked to the "Y"-group via either the C-atom or the O-atom.

The acid addition salts of the invention are pharmaceutically acceptable salts of the compounds of Formula i formed with non-toxic acids. Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, manrelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids.

The compounds of the invention have been found to be potent sigma receptor ligands displacing tritiated di-tolyl guanidine (DTG) from sigma sites in vitro with high potencies, i.e. for many of the compounds with $IC_{50}$ values below 1 nM. Furthermore, many of the present compounds have proven to be very selective ligands for sigma receptors. For example with respect to $\alpha_1$ adrenoceptors and dopamine D-2, serotonin $5\text{-HT}_{1A}$ and $5\text{-HT}_2$ receptors, ratios of binding $IC_{50}$ values (alpha/sigma, dopamine/sigma, $5\text{-HT}_{1A}$/sigma, and $5\text{-HT}_2$/sigma, respectively) of 100→1000 have been found.

The compounds of the invention have the further advantage that the salts thereof have a good water solubility. Furthermore, due to the fact that they are symmetrical dimers, some obvious advantages are obtained in the manufacture of the compounds.

Accordingly, the dimeric piperidine, 1,2,3,6-tetrahydropyridine, and piperazine compounds of the present invention are useful in the treatment of anxiety, psychosis, epilepsy, convulsion, movement disorders, motor disturbances, amnesia, cerebrovascular diseases, senile dementia, e.g. of the Alzhemer type, and Parkinson's disease.

One preferred subgroup of the compounds of the invention comprises the compounds of Formula I wherein $Z^1$ and Y are not linked together and $Z^2$ is $(CH_2)_p$ where p=0, i.e. 4-phenyl-piperidine, -1,2,3,6-tetrahydropyridine, and -piperazine compounds.

Another preferred subgroup comprises compounds of Formula I wherein $Z^1$ and Y are linked together thereby forming a spirocyclic ring system.

In Formula I the following are preferred definitions of the symbols:

n is 1,2 or 3;

X is $(CH_2)_m$, m being 0 or 1, X is $NR^7$, $R^7$ being lower alkyl, cycloalkyl or optionally substituted phenyl, or X is S, O or $CR^8R^9$, wherein $R^8$ is hydroxy or optionally substituted phenyl and $R^9$ is hydrogen;

$R^2$–$R^4$ are independently selected from hydrogen, halogen, lower alkyl and trifluoromethyl;

$R^5$ and $R^6$ are hydrogen

And if $Z^1$ and Y are linked together in order to form a spirocyclic ring system, $Z^1$ is $(CH_2)_q$, q being 1,2 or 3, $CH_2O$, $(CH_2)_2O$, CH=CH, O, S or $CH_2S$; and $Z^2$ is $(CH_2)_p$ wherein p is 0 or 1, or O.

Especially preferred spiropiperidine compounds of Formula I are those wherein $Z^2$ is $(CH_2)_p$, p being 0, $Z^1$ is $(CH_2)_q$, q being 1,2 or 3, $CH_2O$, $(CH_2)_2O$, CH=CH, O, S or $CH_2S$, in particular $CH_2O$, $CH_2S$ or $(CH_2)_2O$.

Particularly preferred compounds are:

1,4-Bis[spiro[isobenzofuran-1(3 H),4'-piperidin]-1'-yl] butane;

1,4-Bis[4-(4-fluorophenyl)piperidin-1-yl]butane;

1,4-Bis[4-(4-fluorophenyl)piperazin-1-yl]butane;

1,6-Bis[spiro[isobenzofuran-1(3 H),4'-piperidin]-1'-yl] hexane;

1,4-Bis[6-fluoro-spiro[isobenzofuran-1(3 H),4'-piperidin] -1'-yl]butane;

1,5-Bis[spiro[isobenzofuran-1(3 H),4'-piperidin]-1'-yl] pentane;

1,4-Bis[spiro[isobenzothiophene-1(3 H),4'-piperidin]-1'-yl]butane;

1,4-Bis[spiro[1-benzopyran-2,4'-piperidin]-1'-yl]butane;

1,4-Bis[spiro[1-benzopyran-4,4'-piperidin]-1'-yl]butane;

1,3-Bis[spiro[isobenzofuran-1-(3 H),4'-piperidin]-1'-yl]propane;

1,3-Bis[4-(4-fluorophenyl)piperidin-1-yl]propane;

1,2-Bis[spiro[isobenzofuran-1(3 H),4'-piperidin]-1'-yl]ethane;

1,2-Bis[4-(4-fluorophenyl)piperidin-1-yl]ethane;

N,N-Bis[2-spiro[isobenzofuran-1(3 H),4'-piperidin]-1-ylethyl]-N-cyclopentylamin;

1,4-Bis[4-(4-fluorophenyl)-1,2,3,6-tetrahydropyridin-1-yl]butane;

N,N-Bis[2-[4-(4-fluorophenyl)piperidin-1-yl]ethyl] aniline;

1,5-Bis[spiro[isobenzofuran-1(3 H),4'-piperidin]-1'-yl]-3-(4-fluorophenyl)pentane;

Bis[2-spiro[isobenzofuran-1(3 H),4'-piperidin]-1'-ylethyl]sulphide, difumarate;

In another aspect the present invention relates to a pharmaceutical composition comprising at least one novel dimeric piperidine, 1,2,3,6-tetrahydropyridine, or piperazine compounds having the above defined general Formula I or a pharmaceutically acceptable acid addition salt or prodrug thereof in combination with one or more pharmaceutically acceptable carriers or diluents.

The pharmaceutical compositions of this invention may be administered by any suitable route, for example orally in the form of tablets, capsules, powders, syrups, etc., or parenterally in the form of solutions for injection. For preparing such compositions methods well known in the art may be used, and any pharmaceutically acceptable carriers, diluents, exipients, or other conventional additive in the art may be used.

Conveniently, the compounds of the invention are administered in unit dosage form s containing said compound in an amount of about 0.01 to 50 mg.

The total daily dose usually ranges from about 0.05 to 100 mg, preferably about 0.1–50 mg of the active compound of the invention.

In a further aspect the present invention relates to the use of dimeric piperidine, 1,2,3,6-tetrahydropyridine, and piperazine compounds having the above defined general Formula I or acid addition salts or prodrugs thereof for the manufacture of a pharmaceutical preparation for the treatment of anxiety, psychosis, epilepsy, convulsion, movement disorders, motor disturbances, amnesia, cerebrovascular diseases senile dementia of the Alzhemer type or Parkinson's disease.

The movement disorders and motor disturbances which may be treated by the preparation according to the invention are e.g. dystonia and tardive dyskinesia and motor disturbances associated with Huntington's chorea or Tourotto's syndrome. Dystonia may be acute or tardive and may be caused by neuroleptics or have another reason.

Cerebrovascular diseases are such disorders caused by cerebral infarction, cerebral hemorrhage, cerebral arteriosclerosis, subarachnoid hemorrhage, cerebral thrombosis, cerebral embolism, or the like, e.g. ischemia.

The compounds of Formula I may be prepared by a) reducing the amide carbonyl groups of a compound of Formula II

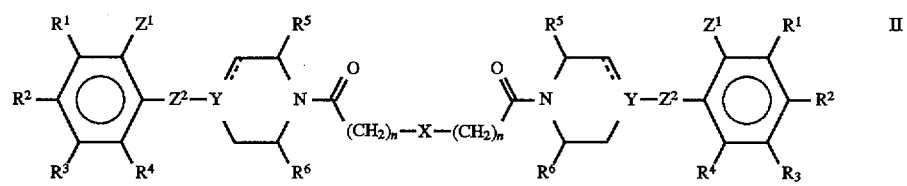

wherein n is 0–4, X, Y, $R^1$–$R^6$, $Z^1$, $Z^2$ and the dotted lines are as previously defined;

b) reducing the amide carbonyl group a of compound of Formula III

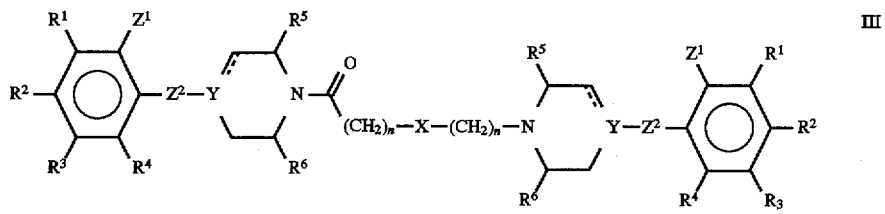

wherein n is n-1, and n, X, Y, $R^1$–$R^6$, $Z^1$, $Z^2$ and the dotted lines are as previously defined;

c) alkylating a compound of formula IV

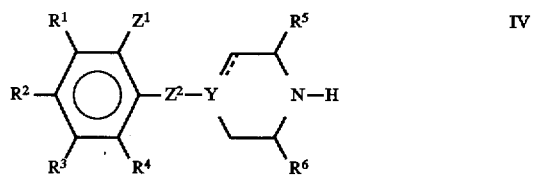

wherein Y, $R^1$–$R^6$, $Z^1$, $Z^2$ and the dotted lines are as previously defined; with epichlorohydrin or an alkylating reagent of the formula V $$A-(CH_2)_n-X-(CH_2)_n-A \qquad V$$

wherein X and n are as previously defined and A is a suitable leaving group such as halogen, mesylate or tosylate;

d) reductive alkylation of an amine of Formula IV with a dialdehyde of the Formula VI or a dicarboxylic acid of the formula VII $$OHC-(CH_2)_n-X-(CH_2)_n-CHO \qquad VI$$

$$HOOC-(CH_2)_n-X-(CH_2)_n-COOH \qquad VII$$

wherein n is 0 to 4, and X is as previously defined; or e) reducing the double bonds in a compound of Formula I in order to obtain the corresponding saturated compound of Formula I. Such double bonds are present when the dotted line represents a bond and/or when $Z^1$ and Y are linked together in order to form a spiropiperidine compound and $Z^1$ comprises a double bond whereupon the compound of Formula I formed is isolated as the free base or a pharmaceutically acceptable acid addition salt thereof.

The reduction according to method a) may preferably be carried out in an inert organic solvent such as diethyl ether or tetrahydrofuran with reducing agents such as eg. lithium aluminium hydride. $AlH_3$ or diborane at appropriate temperatures which are generally from room temperature to reflux temperature. Reductions of amides according to method b) are performed similarly.

Alkylation of compounds of Formula IV according to method c) is conveniently performed in an inert organic solvent such as an alcohol or a ketone with a suitable boiling point, preferably in the presence of a base (potassium carbonate or triethyl amine) at reflux temperature. Epichlorohydrin is a particularly useful reagent for introducing a propylene chain substituted with hydroxy. i.e. for obtaining componds of Formula I wherein n is 1 and X is CHOH.

Reductive alkylation according to method d) is performed by standard literature procedures. The aldehydes VI and carboxylic acids VII are either commercially available or are prepared according to standard procedures.

Reduction of double bonds according to method e) is generally performed by catalytic hydrogenation using Pd or Pt as catalysts in protic solvents such as ethanol or methanol under acidic conditions.

The alkylating reagents V are either commercially available or may be prepared according to well known methods oxidizing either the corresponding alcohols or reducing the carboxylic acids or appropriate derivatives thereof.

The diamides of Formula II are conveniently prepared by treating the 1-unsubstituted derivatives IV with a suitable activated dicarboxylic acid derivative such as proper carboxylic acid chlorides or anhydrides according to known methods. The carboxylic acid derivatives are either commercially available or prepared according to standard procedures. Intermediate mono-amides III are similarly prepared by reaction of an co-halo substituted carboxylic acid via its activated form, such as the acid chloride or anhydride. The latter reaction might be performed in a two step sequence: first reacting the activated acid part with one mole of compounds IV followed by reaction of the co-halo part of the spacer group with another mole of IV. These reactions are performed under standard acylation/alkylation conditions.

4-Phenylpiperidines of formula IV (Y=C and the dotted line indicating no bond) are either commercially available or prepared as described in eg. U.S. Pat. No. 2,891,066; McElvain etal. J.Amer.Chem.Soc. 1950, 72, 3134; Bally et al Chem. Ber. 1887, 20,. The corresponding 4-phenyl-1,2,3,6-tetrahydropyridines of formula IV (Y=C and the dotted line indicating an extra bond) are prepared from N-protected 4-piperidones by addition of properly substituted phenyl lithium or phenyl magnesium halides followed by acid catalyzed water elimination. The N-protecting group (carbamate, benzyl, sulphonyl, acetyl) is finally removed in a conventional manner. The 3-phenyl-8-azabicyclo[3,2,1] oct-2-ene derivatives were prepared accordingly from N-protected 8-azabicyclo[3,2,1]octan-3-ones. 4-Phenylpiperidines are also conviniently prepared by catalytic hydrogenation of the corresponding 4-phenyl-1,2,3,6-tetrahydropyridines using Pt as catalyst.

4-Phenylpiperazines of formula IV (Y=N and the dotted line indicating no bond) are either commercially available or prepared according to the methods in Martin et al. *J. Med. Chem.* 1989, 32, 1052–1056. These methods include ring-closure reaction of properly substituted anilines with bis-(2-chloroethyl)amine (eventually N-protected) by refluxing in highboiling solvents as eg. chlorobenzene typically for some days (2–3), eventually followed by deprotection of an optional N-protection group according to standard procedures.

The spiropiperidine derivatives of Formula IV wherein $Z^1$ and Y are linked together and Y is carbon are prepared as follows:

Spiro[isobenzofuran-1(3 H),4'-piperidine] according to the method described by Marxer et al, *J. Org. Chem.* 1975, 40, 1427. In a corresponding manner spiro[iso-benzofuran-1(3 H),3'14 8'-azabicyclo[3',2',1']octane] was prepared from N-methyl-8-azabicyclo[3,2,1]octan-3-ones;

2,3-Dihydro-spiro[1 H-indene-1,4'-piperidine]and 3,4-dihydro-spiro[naphtalene-1-(2 H),4'-piperidine] following a modification of the method of *J. Med. Chem.*, 1992, 35(11), 2033–2039 and French Patent. No. 1,335,831;

1'-Methyl-spiro[benzo[c]thiophene-1(3 H),4'-piperidine] according to the method is described by Parham et al, *J. Org. Chem.* 1976, 41, 2628. The corresponding demethylated derivative was obtained by treatment with ethyl chloroformate followed by alkaline hydrolysis of the intermediary ethyl carbamate;

1'-Phenylmethyl-spiro[1 H-2-benzopyran-4(3 H),4'-piperidine] according to the method described by Yamamoto et al, *J. Med. Chem.*, 1981, 24, 194. The corresponding debenzylated derivative is obtained by hydrogenation in the presence of a palladium catalyst;

3,4-Dihydro-1'-phenylmethyl-spiro[2 H-2-benzopyran-1, 4'-piperidine] and 3,4-dihydro-1'-phenylmethyl-spiro[1 H-1-benzopyran-2,4'-piperidine] according to the method described by Yamamoto et al, *Chem. Pharm. Bull.* 1981, 29, 3494. The corresponding debenzylated derivative is obtained by treatment with ethyl chloroformate followed by alkaline hydrolysis of the intermediary ethyl carbamate;

1'-Phenylmethyl-spiro[2 H-1-benzopyran-2,4'-piperidine] is obtained according to the method described by Yamamoto et al, *Chem. Pharm. Bull.* 1981, 29, 3494. The corresponding debenzylated derivative is obtained by hydrogenation in the presence of a palladium catalyst;

1'-Phenylmethyl-spiro[3 H-2-benzopyran-3,4'-piperidine]-1(4 H)-one according to the method described by Yamamoto et al, *J. Med. Chem.* 1981, 24, 194. Reduction with lithium aluminium hydride followed by treatment with phosphoric acid according to the procedure described by Marxer et al, *J. Org. Chem.* 1975, 40, 1427 yields 1,4-dihyro-1'-phenylmethyl-spiro[3 H-2-benzopyran-3,4'-piperidine] which is debenzylated by hydrogenation in the presence of a palladium catalyst;

1'-Benzyl-spiro[4 H-1-benzopyran-4,4'-piperidine] is obtained by a method which is analogeous to the one described in EP-A1-0 414 289 for the synthesis of 1'-benzyl-1,4-dihydrospiro[naphthalene-1,4'-piperidine]. Hydrogenation in the presence of a Pd catalyst gave 2,3-dihydrospiro[4 H-1-benzopyran-4,4'-piperidine];

Spiro[1,3-benzodioxole-2,4'-piperidine] is obtained by refluxing 1-ethoxycarbonyl-4-piperidinone and catechol in toluen solution in the presence of p-toluenesulphonic with continous removal of water followed by removal of the benzyl group by hydrogenation in the presence of a palladium catalyst.

The substituents $R^1$–$R^6$ are introduced by applying suitably substituted starting compounds to methods analogously to the above mentioned.

In the following the invention is further illustrated by some examples which, however, may not be construed as limiting.

Melting points are determined on a Büchi SMP-20 apparatus and are uncorrected. $^1$H NMP spectra are recorded at 250 MHz on a Bruker AC 250 spectrometer. Deuterated chloroform (99,8% D), deuteriumoxide (99,9% D) or dimethylsulfoxide (99,9% D) were used as solvents. TMS was used as internal reference standard. Chemical shift values are expressed in ppm values. The following abbreviations are used for multiplicity of NMR signals: s=singlet, d=doublet, t=triplet, q=quartet, p=pentet, dd=double doublet, dt=double triplet, tt=triplet of triplets, m=multiplet.

EXAMPLE 1 (method a)

1,4-Bis[spiro[isobenzofuran-1(3 H),4'-piperidin]-1'-yl]butane 1a.

To a solution of spiro[isobenzofuran-1(3 H),4'-piperidine](3 g) in dichloromethane (25 ml) was added triethylamine (3 ml). The mixture was cooled to 5° C. and a solution of succinic acid dichloride (1 g) in dichloromethane (10 ml ) was added dropwise during ½ h. After stirring for an additional hour at room temperature the mixture was eluted through silica gel with dichloromethane. The diamide was retained by the silica gel and was subsequently extracted from the gel with a mixture of ethyl acetate and THF (1:1). The solvents were evaporated in vacuo and the remaining solid product was recrystallized from diethyl ether. Yield: 2.8 g. Mp 12° C. To a suspension of LiAlH$_4$ (3 g) in dry THF (150 ml) was added in small portions all of the diamide (2.8 g) prepared above. The temperature was slowly raised to reflux and kept there for 2 hours. After cooling to below 10° C. excess of LiAlH$_4$ was destroyed by cautious addition of concentrated aqueous NaOH solution (3 ml) and water (15 ml). Inorganic salts were filtered off and the solvents evaporated in vacuo. The remaining solid product was stirred with diethyl ethyl and the crystalline title compound la was filtered off and dried. Yield 1.4 g. Mp 128° C. 1 H NMR (CDCl$_3$) δ1.55–1.65 (m,4 H), 1.80 (d,4 H), 2.00 (dt,4 H), 2.45 (t,4 H), 2.45–2.55 (m,4 H), 2.95 (broad d,4 H), 5.05 (s, 4 H), 7.10–7.30 (m,8 H).

In a similar way the following compounds were prepared:

1,4-Bis[4-(4-fluorophenyl)piperidin-1-yl]butane 1b, mp 124° C. $^1$H NMR (CDCl$_3$) δ 1.55–1.60 (m,4 H), 1.70–1.85 (m,6 H), 2.05 (dt,4 H), 2.40 (broad t,4 H), 2.45 (tt,2 H), 6.95 (t, 4 H), 7.20 (dd,4 H);

1,4-Bis[1,4-dihydro-spiro[2-benzopyran-3,4'-piperidin]-1'-yl]butane 1c, mp 147°–148° C. $^1$H NMR (CDCl$_3$) δ1.50–1.60 (m,4 H), 1.65 (dr,4 H), 1.80 (broad d,4 H), 2.35–2.45 (m,8 H), 2.55–2.65 (m,4 H), 2.65 (s,4 H), 4.75 (s,4 H), 6.95–7.20 (m,8 H);

1,5-Bis[4-(4-fluorophenyl)piperidin-1-yl]pentane, 2.5 fumarate 1d, mp 176° C. 1 H NMR (DMSO-d$_6$) δ1.35 (broad p,2 H), 1.65 (broad p,4 H), 1.80–1.90 (m,8 H), 2.50–2.70-(m,6 H), 2.75 (t,4 H), 3.30 (d,4 H), 6.55 (s,5 H), 7.10 (t,4 H), 7.25 (dd, 4 H);

1,4-Bis[4-(4-fluorophenyl)piperazin-1 -yl]butane 1e, mp 156°–158° C. $^1$H NMR (CDCl$_3$) δ1.60 (broad p,4 H), 2.45 (broad t,4 H), 2.60 (t,8 H), 3.15 (t,8 H), 6.85–7.00 (m,8 H); 1,6-Bis[spiro[isobenzofuran-1(3 H),4'-piperidin]-1'-yl] hexane 1f, mp 9920 –102° C. $^1$H NMR (CDCl$_3$) δ1.35 (broad p,4 H), 1.60 (broad p,4 H), 1.80 (d,4 H), 2.00 (dr,4 H), 2.35–2.55 (m,8 H), 2.85 (broad d,4 H), 5.05 (s,4 H), 7.15–7.30 (m,8 H); 1,4-Bis[6-fluoro-spiro[isobenzofuran-1(3 H),4'-piperidin]-1'-yl]butane 1 g, mp 134°–135° C. $^1$H NMR (CDCl$_3$) δ1.55–1.65 (m,4 H), 1.75 (d,4 H), 2.00 (dt,4 H), 2.40 (dt, 4 H), 2.40–2.50 (m,4 H), 2,90 (broad d,4 H), 5.05 (s, 4 H), 6.80 (dd.2 H), 6.95 (dt.2 H), 7.15 (dd,2 H);

1,5-Bis[spiro[isobenzofuran-1(3 H),4'-piperidin]-1'-yl] pentane tetrafumarate 1 h, mp 156°–157° C. $^1$H NMR (DMSO-d$_6$) δ1.35 (broad p,2 H), 1.60–1.80 (m,8 H), 2.25 (dt,4 H), 2.80–2.95 (m,8 H), 3.25 (broad d,4 H), 5.05 (s,4 H), 7.20–7.35 (m,8 H);

1,4-Bis[spiro[1,3-benzodioxol-2,4'-piperidin]-1'-yl] butane 1I, mp 164°–167° C. $^1$H NMR (CDCl$_3$) δ1.60 (broad p,4 H), 2.15 (t,8 H), 2.50 (t,4 H), 2.70 (t,8 H), 6.85 (s, 8 H);

1,4-Bis[6-(trifluoromethyl)-spiro[isobenzofuran-1(3 H),4'-piperidin]-1-yl]butane, dihydrochloride 1j, mp 305°–310° C. $^1$H NMR (DMSO-d$_6$) δ1.70–1.95 (m,8 H), 2.30–2.50 (m,4 H), 3.05–3.60 (m,12 H), 5.05 (s,4 H), 7.45 (broad s,2 H), 7.65 (d,2 H), 7.75 (d,2 H);

1,4-Bis[1,3-dihydro-spiro[2-benzopyran-4,4'-piperidin]-1'-yl]butane 1k, mp 173°–176° C. $^1$H NMR (CDCl$_3$) δ1.55 (p,4 H), 1.75 (d,4 H), 2.05–2.20 (m,8 H), 2.45 (t,4 H), 2.90 (d,4 H), 3.90 (s,4 H), 4.80 (s,4 H), 6.95 (d,2 H), 7.15 (t,2 H), 7.25 (t,2 H), 7.50 (d,2 H);

1,4-Bis[5-methyl-spiro[isobenzofuran-1(3 H),4'-piperidin]-1'-yl]butane 1l, mp 149°–151° C. $^1$H NMR (CDCl$_3$) δ1.55 (p,4 H), 1.75 (d,4 H), 1.95 (dr,4 H), 2.90 (s, 6 H), 2.35–2.50 (m,8 H), 2.85 (d,4 H), 5.05 (s,4 H), 6.95–7.10 (m,6 H);

1,4-Bis[7-fluoro-spiro[isobenzofuran-1(3 H),4'-piperidin]-1'-yl]butane 1m, mp 175°–179° C. $^1$H NMR (CDCl$_3$) δ1.55–1.65 (m,4 H), 1.80 (d,4 H), 2.00 (dr,4 H), 2.30–2.50 (m,16 H), 2.90 (broad d,4 H), 5.05 (s, 4 H), 6.90–7.00 (m,4 H), 7.20–7.25 (m,2 H);

1,4-Bis[spiro[isobenzofuran-1(3 H),3'-8'-azabicyclo[3', 2',1']octan]-8'-yl]butane 1n, mp 175–179° C. $^1$H NMR (CDCl$_3$) δ1.65 (p,4 H), 1.90 (d,4 H), 1.95–2.05 (m,4 H), 2.15 (dd,4 H), 2.15–2.30 (m,4 H), 2.50 (broad s,4 H), 3.30 (broad s,4 H), 5.05 (s,4 H), 7.10–7.30 (m,8 H);

1,4-Bis[3-(4-fluorophenyl)-8-azabicyclo[3,2,1]oct-2-en-8-yl]butane 1o, mp 163°–165° C. $^1$H NMR (CDCl$_3$) δ1.55–1.65 (m,6 H), 1.90 (dt,2 H), 1.95–2.25 (m,6 H), 2.55 (broad t,4 H), 2.80 (dd,2 H), 3.50 (broad t,4 H), 6.20 (d,2 H), 7.00 (t,4 H), 7.30 (dd,4 H);

1,4-Bis[spiro[1-benzopyran-2,4'-piperidin]-1-yl]butane, difumarate 1p, mp 192°–198°0 C. $^1$H NMR (DMSO-d$_6$) δ1.55–1.65 (m,4 H), 1.80–2.05 (m,8 H), 2.60–2.80 (m,8 H), 2.80–2.95 (m,4 H), 5.75 (d,2 H), 6.50(d,2 H). 6.55 (s,4 H), 6.80–6.90 (m,4 H), 7.10–7.20 (m,4 H);

1,4-Bis[3,4-dihydro-spiro[naphthalene-1(2 H),4'-piperidin]-1'-yl]butane 1q, mp 167°–175° C. $^1$H NMR (CDCl$_3$) δ1.55–1.70 (m,8 H), 1.70–1.90 (m,8 H), 2.20 (dr,4 H), 2.20–2.35 (m,4 H), 2.45 (broad t,4 H), 2.75–2.90 (m,8 H), 7.00–7.20 (m,6 H), 7.55 (d,2 H), 1,4-Bis[3,4-dihydro-spiro[1-benzopyran-2,4'-piperidin]-1-yl]butane, difumarate 1r, mp 202°–204° C. $^1$H NMR (DMSO-d$_6$) δ1.50–1.60 (m,4 H), 1.70–1.90 (m,12 H), 2.60–2.80 (m,12 H), 2.80–2.95 (m,4 H), 6.55 (s,4 H), 6.70–6.90 (m,4 H), 7.05–7.20 (m, 4 H);

1,4-Bis[spiro[isobenzothiophene-1(3 H),4'-piperidin]-1-yl]butane 1s, mp 155°–160° C. $^1$H NMR (CDCl$_3$) δ1.55–1.65 (m,4 H), 1.90–2.00 (m,4 H), 2.15–2.30 (m,8 H), 2.45 (broad t,4 H),3.00–3.10-2.55 (m,4 H), 4.15 (s, 4 H), 7.25 (s,8 H);

1,4-Bis[spiro[1-benzopyran-2,4'-piperidin]-1-yl]butane, 1.25 fumarate 1t, mp 226–230° C. $^1$H NMR (D$_2$O) δ1.90 (broad s,4 H), 2.15–2.45 (m,8 H), 2.90 (t,4 H), 3.20–3.65 (m,12 H), 3.95 (t,4 H), 6.65 (s,2.5 H), 7.15–7.40 (m,8 H);

1,4-Bis[spiro[1-benzopyran-4,4'-piperidin]-1'-yl]butane, 1u, mp 163°–165° C. $^1$H NMR (CDCl$_3$) δ1.50–1.65 (m,8 H), 1.95 (t,4 H), 2.10–2.25 (m,8 H), 2.40 (t,4 H), 2.75–2.90 (m,4 H), 4.10 (t,4 H), 6.80 (dd,2 H), 6.90 (dt, 2 H), 7.05 (dt,2 H) 7.40 (dd,2 H).

EXAMPLE 2 (method b)

1,3-Bis[spiro[isobenzofuran-1(3 H),4'-piperidin]-1'-yl]propane difumarate 2a.

To a solution of spiro[isobenzofuran-1(3 H),4'-piperidine] (1.9 g)in dichloromethane (40 ml) was added triethylamine (2.3 ml). After cooling to 10° C. a solution of 3-chloropropionic acid chloride (1.7 g) in dichloromethane (15 ml) was added dropwise during 10 min. The mixture was stirred at room temperature for another hour. The 1'-(3-chloropropanoyl)-spiro[isobenzofuran-1(3 H),4'-piperidine] was purified by subjecting the reaction mixture to column chromatography on silica gel (eluted with ethyl acetate/heptane 60:40). Yield 1.8 g as an oil. As a result of elimination of hydrogen chloride 1'-(2-propenoyl)-spiro [isobenzofuran-1(3 H),4'-piperidine] was isolated as a by-product. Yield 0.7 g as an oil. Both the 3-chloropropanoic acid amide and the propenoic acid amide were dissolved in methyl isobutyl ketone (MIBK) (40 ml). To this solution K$_2$CO$_3$ (1.5 g) and spiro[isobenzofuran-1(3 H), 4'-piperidine] (1.8 g) were added. The resulting mixture was refluxed overnight. Inorganic salts were subsequently filtered off and MIBK evaporated in vacuo. The resulting 1,3-bis[spiro[isobenzofuran-1(3 H),4'-piperidin]-1'-yl] propanoic acid amide was purified by column chromatography on silica gel (eluted with ethyl acetate containing 4% of triethylamine). Yield 2.2 g as a viscous oil. To a suspension of LiAlH$_4$ (0.8 g) in dry THF was added all of the above isolated mono-amide (2.2 g) in THF solution (25 ml). The resulting mixture was refluxed for 2 hours. Excess LiAlH$_4$ was destroyed by cautiously adding concentrated aqueous NaOH (1 ml) at 10° C. followed by addition of water (5 ml). Inorganic salts were filtered off and THF was evaporated in vacuo. The remaining oil was dissolved in ethanol (15 ml) and fumaric acid was added (1.1 g). Upon heating to 60° C. the fumaric acid salt of the title compound 2a crystallized. Yield 2.2 g. Mp 232°–233° C. $^1$H NMR (DMSO-d$_6$) δ1.70 (d,4 H), 1.95 (broad p,2 H), 2.10 (dt,4 H), 2.65 (t,4 H), 2.70–2.80 (m,4 H), 3.15 (broad d,4 H), 5.00 (s, 4 H), 6.55 (s,4 H), 7.20–7.35 (m,8 H).

In a similar way the following compounds were prepared:

1,3-Bis[4-(4-fluorophenyl)piperidin-1-yl]propane 2b, mp 59°–61° C. $^1$H NMR (CDCl$_3$) δ1.75–1.90 (m,10 H), 2.05 (dt,4 H), 2.45 (t,4 H), 2.45–2.55 (m,2 H), 3.05 (broad d,4 H), 6.95 (t, 4 H), 7.20 (dd,4 H);

1,2-Bis[spiro[isobenzofuran-1(3 H),4'-piperidin]-1'-yl] ethane 2c, mp 152°–153° C. $^1$H NMR (CDCl$_3$) δ1.80 (d,4 H), 2.00 (dr,4 H), 2.50 (dt,4 H), 2.65 (s,4 H), 2.90 (broad d,4 H), 5.05 (s, 4 H), 7.10–7.30 (m,8 H);

1,2-Bis[4-(4-fluorophenyl)piperidin-1-yl]ethane 2d, mp 151°–154° C. $^1$H NMR (CDCl$_3$) δ1.70–1.85 (m,8 H), 2.10 (dr,4 H), 2.45–2.55 (m,2 H), 2.60 (s, 4 H), 3.05 (broad d,4 H), 6.95 (t, 4 H), 7.15 (dd,4 H).

EXAMPLE 3 (method a)

N,N-Bis[2-spiro[isobenzofuran-1(3 H),4'-piperidin]-1'-ylethyl]-N-cyctopentylamine, trihydrochloride 3a.

To a solution of spiro[isobenzofuran-1(3 H),4'-piperidine] (14 g) in dichloromethane (160 ml) triethylamine (11 ml) was added. After cooling to 10° C. a solution of chloroacetylchloride (8 ml) in dichloromethane (10 ml) was added dropwise during 20 minutes. The reaction mixture was finally allowed to reach room temperature. The mixture was subsequently filtered through silica gel (eluted with ethyl acetate/n-heptane 60:40) affording 12 g of the α-chloroacetamide derivative. A mixture of the thus obtained α-chloroacetamide derivative (1.4 g) and cyclopentylamine in MIBK (25 ml) was refluxed for 2 h. The solvent was evaporated in vacuo and the cyclopentylamino derivative was extracted from an alkaline (pH>9) aqueous solution with ethyl acetate. The organic phase was worked up as above yielding 2.0 g of the α-(cyclopentylamino) acetamide derivative as a viscous oil. To a solution of the α-(cyclopentylamino)acetamide derivative (2 g) in MIBK 1'-chloracetyl-spiro[isobenzofuran-1(3 H),4'-piperidine] (1.4 g) and potassium carbonate (1 g) were added. The mixture was refluxed for 3 h. After cooling to room-temperature the mixture was filtered through silica gel (eluted with 4 % triethylamine in ethyl acetate. Evaporation of the solvents afforded 2.4 g of the diamide which was reduced with LiAlH$_4$ as described in example 1. The title compound 3a crystallized from a mixture of ethanol and acetone (1:4). Yield 1.3 g, mp 258°–260° C. $^1$H NMR (DMSO-d$_6$) δ1.50–2.45 (m,16 H), 3.25–3.80 (m,17 H), 5.05 (s,4 H), 7.10–7.40 (m, 8 H).

In a similar way the following compound was prepared:

N,N-Bis[2-spiro[isobenzofuran-1(3 H),4'-piperidin]-1'-ylethyl]-N-methylamine, trihydrochloride 3b. Mp 265°–266° C. $^1$H NMR (DMSO-d$_6$) δ1.90 (d,4 H), 2.50°–2.90 (m,7 H), 3.25 (t,4 H), 3.50–3.90 (m,12 H), 5.05 (s,4 H), 7.15–7.40 (m,8 H).

EXAMPLE 4 (method a)

1,4-Bis[spiro[ind-2-en-1,4'-piperidin]-1'-yl]butane 4a.

The following method is adapted from a method in J. Med. Chem. 1992, 35 (11), 2033–2039. A solution of inden (18 ml) in dry THF (75 ml) was cooled to 0° C. and lithium bis(trimethylsilyl)amide (300 ml solution) was added dropwise during 20 minutes. After stirring for ½ h at 0° C. a solution of N-t-butyloxycarbonyl-N,N-bis(2-chloroethyl) amine (36 g) in dry THF (100 ml) was added during ½ h with ice cooling. After 2 h stirring at 0° C. the solvents were evaporated in vacuo. The remaining oil was subjected to column chromatography (eluted with heptane/diethyl ether 80:20) affording 19 g of the t-butyloxycarbonyl spiropiperidine derivative as a pure oil. Deprotection of the spiropiperidine was achieved by adding t (14 g) cautiously to trifluoroacetic acid (75 ml) at room temperature. Excess trifluoroacetic acid was evaporated in vacuo. The remaining viscous oil was dissolved in dichloromethane (150 ml) and triethyl amine (30 ml) was added. At 0°–5° C. succinic acid dichloride (3.1 g)in dichloromethane (15 ml) was added dropwise. The mixture was finally stirred for an hour at room temperature. Water (500 ml) and hydrochloric acid (pH <1) were added. The organic phase was worked-up leaving the diamide as an oil (11.6 g). A solution of the diamide (11 g) in dry THF (100 ml) was added dropwise to a suspension of LiAlH$_4$ (5 g) in dry THF (100 ml) during ½ h at 40–50%. After refluxing for 2 h the mixture was cooled to 10° C. and conc. aqueous NaOH solution (5 ml) and water (15 ml) were added cautiously. Inorganic salts were filtered off and the solvents were evaporated in vacuo. The title compound 4a was purified by column chromatography on silica gel (eluted with ethyl acetate/ethanol/triethyl amine 90:10:4) and finally crystallized from ethyl acetate. Yield 4.3 g. Mp 121°–122°

C. $^1$H NMR (CDCl$_3$) δ1.40 (broad d,4 H), 1.65 (broad p, 4 H), 2.25 (dt,4 H), 2.35 (t,4 H), 2.55 (broad t,4 H), 3.05 (broad d,4 H), 6.75 (d,2 H), 6.85 (d,2 H), 7.15–7.40 (m,8 H).

EXAMPLE 5 (method e)

1,4-Bis[spiro[indan-1,4'-piperidin]-1'-yl]butane 5a.

To a solution of 1,4-Bis-spiro[ind-2-en-1,4'-piperidin-1'-yl]butane (compound 4a) (3 g) in ethanol (90 ml) were added acetic acid (5 ml) and 5% palladium on carbon (0.9 g). The mixture was hydrogenated in a Parr apparatus for 2 hours ar 3 atm. The catalyst was filtered off and the solvent evaporated. The remaining oil was solved in diluted aqueous NH$_4$OH (200 ml, pH>9). The title compound 5a was extracted with ethyl acetate and worked-up as above and finally crystallized from ethyl acetate. Yield 1.6 g. Mp 113°–115° C. $^1$H NMR (CDCl$_3$) δ1.55–1.65 (m,8 H), 1.95–2.10 (m,8 H), 2.15 (t,4 H), 2.45 (broad s,4 H). 2.95 (t,8 H), 7.10–7.30 (m,8 H).

EXAMPLE 6

1,4-Bis[4-(4-fluorophenyl)-1,2,3,6-tetrahydropyridin-1-yl]butane 6a

To a solution of piperidin-4-ethylene ketal (7 g) (commercially available) and triethylamine in dichloromethane (50 ml) was added dropwise succininc acid dichloride (3.1 g) in dichloromethane (25 ml) at 10° C. during 15 minutes. After stirring for 1 h at room temperature water (200 ml) was added and the organic phase was subsequently worked-up. The crude crystalline diamide (7.4 g) melted at 120° C. To a suspension of LiAlH$_4$ (20 g) in dry THF (400 ml) a solution of the diamide (70 g)in dry THF (700 ml) was added dropwise at 40° C. during 45 minutes. After refluxing for 2 h the mixture was cooled to 10° C. and conc. aqueous NaOH solution (10 ml) and water (30 ml) were added cautiously. Inorganic salts were filtered off and the solvents were evaporated in vacuo leaving the 1,4obis-(1-piperidino)butane derivative (62 g) as an oil. The ketone group was deprotected by s adding perchloric acid (240 ml) to a solution of the 1,4-bis(1-piperidino)butane derivative (40 g) in dichloromethane at −10° C. The resulting mixture was stirred at room temperature for 70 hours. Ice (2 kg) was added and pH was adjusted to >9 by addition of conc. aqueous NaOH solution. The organic phase was separated and subsequently worked up yielding the 1,4-bis(4-oxopiperidin-1-yl)butane (26 g) as an oil which was used without further purification. A solution of n-butyllithium in hexane (200 ml, 1.6M) was added to dry diethyl ether (200 ml) while cooling. The resulting solution was cooled to −50° C. and a solution of 1-bromo-4-fluorobenzene in dry diethyl ether (200 ml) was added during ½ h at −45° C. After stirring for another ½ h a solution of 1,4-bis(4-oxopiperidin-1-yl)butane (24 g) in dry diethyl ether was added dropwise during 40 minutes. The temperature was finally allowed to raise to 0° C. The mixture was poured onto ice (1.5 kg). To adjust pH<1 dil. hydrochloric acid was cautiously added. The organic phase was separated and discarded. To the acidic aqueous solution was added NH$_4$OH until pH>9. The 1,4-bis[4-(4-fluorophenyl)-4-hydroxypiperidin-1-yl]butane (10 g) was extracted with ethyl acetate (2×50 ml) and isolated as an oil. Water elimination was accomplished by dissolving the obtained piperidin-4-ol derivative (10 g) in trifluoroacetic acid (50 ml) and refluxing for 1 h. After cooling to room temperature the mixture was poured onto ice (2 kg) and ethyl acetate (500 ml). Diluted aqueous NH$_4$OH was added to adjust pH>9 and the organic phase was separated and subsequently worked-up as above. The title compound 6a crystallized from ethyl acetate. Yield 6.1 g. Mp 165°–167° C. $^1$H NMR (CDCl$_3$) δ1.65 (broad p,4 H). 2.45–2.55 (m,8 H), 2.75 (t,4 H), 3.15 (q,4 H), 6.00 (broad s,2 H), 7.00 (t,4 H), 7.35 (dd,4-H).

EXAMPLE 7 (method a)

N,N-Bis[2-[4-(4-fluorophenyl)piperidin-1-yl]ethyl] aniline 7a

To a solution of aniline (49 g) in ethanol (400 ml) sodium acetate (130 g) and ethyl lo bromoacetate (250 g) were added. The mixture was refluxed overnight and was subsequently filtered. The solvents were evaporated in vacuo and the remaining oil was distilled at reduced pressure (12 mmHg). Unreacted ethyl bromoacetate and the mono alkylated aniline were thus distilled off leaving the crude diethyl N,N-anilinodiacetate (31 g) which was used without further purification. To a solution of is this diester (31 g) in ethanol (200 ml) were added KOH (20 g) and water (30 ml). Hydrolysis was accomplished by refluxing for 2 h. Ethanol and water were evaporated in vacuo and the remaining di-potassium salt was dissolved in water (500 ml). Concentrated hydrochloric acid was added to adjust pH<1. The N,N-bis(carboxymethyl)aniline was extracted with ethyl acetate (2×100 ml). The crude product (24 g) resulting after work-up of the organic phase was used without further purification. A mixture of the crude N,N-bis(carboxymethyl) aniline (3,4 g), 4-(4-fluorophenyl)piperidine (6 g), dicyclohexylcarbodiimide (8.5 g), p-toluenesulphonic acid (150 mg) in anh. pyridine (50 ml) was stirred overnight at 25°–30° C. Water (500 ml) and ethyl acetate (300 ml) were added and concentrated hydrochloric acid was cautiously added until pH=3. The organic phase was worked-up as above. The crude diamide was purified by column chromatography on silica gel (eluted with ethyl acetate). Yield 4.2 g, mp 167°–168° C. Reduction of the diamide (4.2 g) with LiAlH$_4$ according to the method described in Example 1 afforded the title compound 7a. Yield 0.9 g. Mp 104°–105° C. (crystallized from diethyl ether). $^1$H NMR (CDCl$_3$) δ1.75–2.00 (m,8 H), 2.20 (dt,4 H), 2.60 (t,4 H), 2.45–2.55 (m,2 H), 3.15 (broad d,4 H), 3.55 (t,4 H), 6.70–6.80 (m,3 H), 7.05 (t, 4 H), 7.20–7.30 (m,6 H).

In a corresponding way the following compound Was prepared from 3-(4-fluorophenyl)glutaric acid dichloride and spiro[isobenzofuran-1(3 H), 4'-piperidine]:

1,5-Bis[spiro[isobenzofuran-1(3 H),4'-piperidin]-1'-yl]-3-(4-fluorophenyl)pentane, difumarate 7b, mp 175°–177° C. $^1$H NMR (DMSO-d$_6$) δ1.70 (d,4 H), 1.80–2.20 (m.8 H), 2.40–2.50 (m,1 H), 2.60–2.80 (m,8 H), 3.10 (broad s,4 H), 5.00 (s, 4 H), 6.55 (s, 4 H), 7.05–7.35 (m,12 H).

EXAMPLE 8 (method a)

Bis[2-spiro[isobenzofuran-1(3 H),4'-piperidin]-1-ylethyl]sulphide, difumarate 8a To a solution of spiro[isobenzofuran-1(3 H)4'-piperidine] (14 g) and triethylamine (12 ml) in dichloromethane (140 ml) cooled to 10° C. a solution of bromoacetyl bromide (7 ml) in dichloromethane (25 ml) was added dropwise during 15 minutes. The mixture was further stirred at room temperature for 45 minutes. The crude s reaction mixture was directly poured onto silica gel and the bromoacetamide of spiro[isobenzofuran-1(3 H),4'-piperidine] was eluted with ethyl acetate/heptane 3:2. Yield 5.6 g. To ethyl thioglycolate (2.4 g) in ethanol (40 ml) was added solid potassium t-butoxide (2.3 g)in small portions. To the resulting potassium ethyl thioglycolate was added the bromoacetamide (3.8 g) from above. The mixture was stirred overnight and the 1'-ethoxycarbonylmethylthiomethylcarbonyl- spiro [isobenzofuran-1(3 H),4'-piperidine] (3.8 g) was worked up by extraction with diethyl ether from water. The ethyl ester (3.8 g) was hydrolyzed to the corresponding 1'-carboxymethylthiomethylcarbonyl-spiro[isobenzofuran-1(3 H),4'-piperidine] (3.2 g) by refluxing with KOH in aqueous ethanol according to the procedure in Example 7. The carboxylic acid (3.1 g) was refluxed with thionylchloride (1.5 ml) and a drop of DMF in dichloromethane (50 ml) for 1 h. Excess of thionylchloride was carefully evaporated twice with n-heptane in vacuo. To a cooled (10° C.) solution of spiro[isobenzofuran-1(3 H),4'-piperidine] (2 g) and triethylamine (2.5 ml) in dichloromethane (40 ml) was added dropwise a solution of the above obtained crude carboxylic acid chloride (3 g) in dichloromethane (25 ml). After stirring for another hour at room temperature the diamide (2.9 g) was isolated by subjecting the crude reaction mixture to column chromatography on silica gel (eluted with ethyl acetate). The total amount of diamide was reduced with LiAlH$_4$ according to the method described in Example 1. Yield 2.2 g. The difumarate salt of the title compound 8a crystallized from ethanol/acetone1:1. Mp 92°–94° C. $^1$H NMR (DMSO-d$_6$) δ1.65 (d,4 H), 2.05 (dt,4 H), 2.65 (t,4 H), 2.85 (s,8 H), 3.05 (d,4 H), 5.00 (s,4 H), 6.60 (s, 4H), 7.20–7.35 (m,8 H).

EXAMPLE 9

Bis[2-spiro[isobenzofuran-1(3 H),4'-piperidin]-1'-ylethyl]sulphone 9a

Bis[2-spiro[isobenzofuran-1(3 H),4'-piperidin-1'-yl]ethyl]sulphide (0.8 g) from Example 8 was dissolved in trifluoroacetic acid (10 ml) and cooled to 0° C. A cold solution of 35% H$_2$O$_2$ (1 ml) in trifluoroacetic acid (4 ml) was added dropwise during 5 minutes. After heating for 1 h at 50° C. the reaction mixture was poured into ethyl acetate (200 ml) and diluted aqueous NH$_4$OH (500 ml) (cooled with ice). The organic phase was separated and worked up as above. The crude product was purified by column chromatography on silica gel (eluted with ethyl acetate/ triethylamine 100:4). The title compund 9a crystallized by stirring with diethyl ether. Yield 0.6 g. Mp 170°–172° C. $^1$H NMR (CDCl$_3$) δ1.80 (d,4 H), 1.95 (dt,4 H), 2.55 (dr,4 H), 2.85 (broad d,4 H), 3.00 (t,4 H), 3.35 (t,4 H), 5.05 (s, 4 H), 7.10–7.30 (m,8 H).

EXAMPLE 10 (method b)

Bis[2-spiro[isobenzofuran-1(3 H),4'-piperidin]-1'-ylethyl]ether,dihydrochloride 10a To spiro[isobenzofuran-1(3 H),4'-piperidine] (15 g) in ethanol (150 ml) was added finely powdered potassium carbonate. Ethyl bromoacetate (10 ml) was added dropwise at 25°–30° C. The mixture was finally stirred at 50°–55° C. for 1 h. Inorganic salts were filtered off and the ethanol evaporated in vacuo. The crude 1'-ethoxycarbonylmethyl-spiro[isobenzofuran-1(3 H),4'-piperidine] was extracted from water with diethyl ether and worked-up as above. Yield 20 g as an oil. The ethyl ester (20 g) was reduced with LiAlH$_4$ according to the method in Example 1 yielding the 1'-(2-hydroxyethyl)-spiro[isobenzofuran-1(3 H),4'-piperidine] (12 g) as an oil. To a suspension of NaH (1.4 g 50% in oil) in dry THF (40 ml) was added dropwise at room temperature a solution of 1'-(2-hydroxyethyl)-spiro [isobenzofuran-1(3 H),4'-piperidine] (6 g) in dry THF (25 ml). Hydrogen gas evolves. After stirring for another 20 minutes a solution of 1'-chloroacetyl-spiro[isobenzofuran-1(3 H),4'-piperidine] (4 g) (prepared as the corresponding bromoacetyl derivative in Example 8) in dry THF was added dropwise at 25°–30° C. After stirring for another 1.5 h the 2-spiro[isobenzofuran-1(3 H),4'-piperidin]-1'-ylethyl spiro [isobenzofuran-1(3 H),4'-piperidin]-1'-ylcarbonylmethyl ether (6 g) was isolated by extraction with ethyl acetate from water and finally purified by column chromatography on silica gel (eluted with ethyl acetate/ethanol/triethylamine 80:20:4). The thus isolated mono-amide (4.5 g) was reduced with LiAlH$_4$ according to the method in Example 2 affording the title compound 10a. The dihydrochloride salt crystalized from acetone. Yield 2.2 g. Mp 141°–143° C. $^1$H NMR (DMSO-d$_6$) δ1.85 (d,4 H), 2.50–2.75 (m,4 H), 3.10–3.70 (m,12 H), 3.85 (broad s,4 H), 5.05 (s,4 H), 7.15–7.40 (m,8 H), 10.60 (broad s.2 H).

EXAMPLE 11 (method c)

1,6-Bis[5-methyl-spiro[isebenzofuran-1(3 H),4'-piperidin]-1-yl]hexane 11 a

A solution of 5-methyl-spiro[isobenzofuran-1 (3 H),4'-piperidine] (4 g), 1,6-dibromohexane (2.2 g), finely powdered potassium carbonate (2.7 g) and a crystal of potassium iodide in MIBK (150 ml) was refluxed for 4 h. Inorganic salts were filtered off and MIBK evaporated. Column chromatography on silica gel (eluted with ethyl acetate/ethanol/ triethylamine 75:25:4) gave the pure title compound 11a. Yield 1.0 g. Mp 113°–116° C. (recrystallized from 2-propyl ether). $^1$H NMR (CDCl$_3$) δ1.30–1.45 (m,4 H), 1.50–1.65 (m,4 H), 1.80 (d,4 H), 2.00 (dt,4 H), 2.35 (s,6 H), 2.45–2.50 (m,8 H), 2.85 (broad d,4 H), 5.05 (s, 4 H), 6.95–7.10 (m,6 H).

EXAMPLE 12 (method c)

1,3-Bis[4-(4-fluorophenyl)piperidin-1-yl]-2-propanol 12a

A mixture of 4-(4-fluorophenyl)piperidine (2.6 g), epichlorhydrine (1.1 ml), potassium carbonate (2.0 g) in MIBK was stirred overnight at room temperature. Inorganic salts were filtered off and the solution was subsequently refluxed for 3 hours. After addition of triethylamine (1 ml) the crude reaction mixture was directly subjected to column chromatography on silica gel (eluted with ethyl acetate/ triethylamine 100:4). The title compound 12a crystallized from 2-propyl ether. Yield 1.2 g. Mp 79°–80° C. $^1$H NMR (CDCl$_3$) δ1.65–1.90 (m,8 H), 2.15 (dt,2 H), 2.35 (dt,2 H), 2.40 (d,4 H), 2.45–2.60 (m,2 H), 3.10 (t, 4 H), 3.95 (p,1 H), 6.95 (t,4 H), 7.15 (dd,4 H).

EXAMPLE 13 (method c)

1,3-Bis[4-(4-fluorophenyl)piperazin-1-yl]-2-propanone 13a

To a solution of 1-(4-fluorophenyl)piperazine (12 g) in acetone (40 ml) kept at reflux temperature a solution of 1,3-dichloroacetone (1.3 g)in acetone (10 ml) was added dropwise. The mixture was refluxed for another 2 hours. Acetone was evaporated in vacuo. The remaining viscous oil was subjected to column chromatography on silica gel (eluted with ethyl acetate/ethanol/triethylamine 80:20:4). The title compound 13a crystallized from diethyl ether. Yield 0.6 g. Mp 106°–107° C. $^1$H NMR (CDCl$_3$) δ2.70 (t,8 H), 3.15 (t,8 H), 3.45 (s, 4 H), 6.85–7.00 (m,8 H).

PHARMACOLOGY

The compounds of the invention were tested by well recognized and reliable test methods as follows.

Inhibition of $^3$H-DTG Binding to Sigma Receptors in Rat Brain in vitro.

By this method the inhibition by drugs of the binding of 2 nM $^3$H-DTG (1,3-di-o-tolyl guanidine) to sigma receptors in homogenates or membranes from rat brain without cerebellum is determined in vitro as modified from Weber et al. *Proc. Natl. Acad. Sci.* 1986, 83, 8784.

Tissue preparations:

Homogenate: Rats (150–250 g) are decapitated and the brains (without cerebellum) quickly removed and placed on ice, weighed and homogenized in 100 vol ice-cold (0° C.) 50 mM Tris-buffer (pH 7.7) in an ethanol rinsed glass/teflon homogenizer at 0° C. and kept on ice until use.

P2-membranes: Brains are homogenized in 10 vol 0.32M sucrose in an ethanol rinsed glass/teflon homogenizer with 10 strokes up and down. The homogenate is centrifuged for 10 min at 900×$g_m$ at 4° C. The supernatant are decanted and centrifuged for 20 min at 50,000 $g_m$ at 4° C. The resulting pellet is resuspended in 10 vol ice-cold 50 nM Tris-buffer (pH 7.7) and incubated for 30 min. at 37° C. The membrane suspension is then centrifuged for further 20 min. at 50,000 $g_m$ at 4° C. The pellet is resuspended in 50 vol. of ice-cold Tris-buffer and used immediately.

Binding analysis:

0.5 ml 50 mM Tris-buffer (pH 7.7), 0.25 ml displacer (6×100 µM DTG, 6×[test compound], or Tris-buffer), and 0.25 ml 6×2 nM $^3$H-DTG are mixed into 5 ml plastic test tubes and kept at 4° C. until use. The binding reaction are initiated by mixing 0.5 ml tissue suspension into this solution and incubate at 25° C. for 20 min. Glass fiber filters (Whatman GF/B) are placed on the filter machine which is then closed tight. Just before filtration vacuum is turned on, and the filters washed with 0.1% PEI solution from a spray bottle followed by one wash with Tris-buffer. The binding reaction is stopped by filtration of the assay mixture at reduced pressure (750 mbar) followed by further 3 washes with 5 ml ice-cold Tris-buffer. The filters are placed in counting vials and 4 ml scintillation solution added. The vials are counted in a Beckmann scintillation counter.

Buffers and solutions:

50 mM Tris-buffer pH 7.7:7.38 g Trizma - 7.7 plus distilled $H_2O$ up to 1 liter. 100 ml 10% polyethylenimin (PEI): 100 ml dest. $H_2O$ is added to approx. 20 g 50% PEI which is solubitized by stirring and heating. Diluted (1+99) before use.

6×2 nM $^3$H-DTG: The exact volume depends on the actual concentration of the batch, but is made as close as possible to 12 nM. The containers for the radioactive solution is rinsed in 96% ethanol before use.

6×100 µM DTG: 14.36 mg/100 ml is kept frozen in 10 ml aliqouts.

$^3$H-DTG was obtained from NEN Research Products, Du Pont Denmark. Specific activity 62.3 Ci/mmol.

The known sigma receptor ligands BMY 14802 and rimcazole were included in the test for comparizon purposes.

TABLE I $^3$H DTG BINDING DATA

| Compound No. | IC$_{50}$ (nM) | Compound No. | IC$_{50}$ nM |
| --- | --- | --- | --- |
| 1a | 0.64 | 1u | 0.17 |
| 1b | 0.41 | 2a | 0.76 |
| 1c | 16 | 2b | 0.17 |
| 1d | 1.4 | 2c | 0.23 |
| 1e | 0.89 | 2d | 0.50 |
| 1f | 0.71 | 3a | 1.5 |
| 1g | 0.44 | 3b | 4.9 |
| 1h | 2.0 | 4a | 4.0 |
| 1i | 45 | 5a | 3.1 |
| 1j | 19 | 6a | 0.31 |
| 1k | 8.7 | 7a | 3.6 |
| 1l | 23 | 7b | 0.72 |
| 1m | 5.1 | 8a | 0.78 |
| 1n | 99 | 9a | 1800 |
| 1o | 74 | 10a | 2.5 |
| 1p | 32 | 11a | 9.7 |
| 1q | 4.0 | 12a | 2.4 |
| 1r | 130 | 13a | 2500 |
| 1s | 0.04 | BMY 14802 | 230 |
| 1t | 0.38 | Rimcazole | 180 |

It is seen from Table I that the compounds used in the present invention are very potent sigma receptor ligands as compared to the reference compounds which are known in the art to be sigma receptor ligands. As seen many of the compounds tested showed ED$_{50}$ values in the area below 1 nM.

Furthermore, the ability of the present compounds in inhibiting the binding of $^3$H-Prazosin to $\alpha_1$ adrenoceptors in membranes from rat brain were determined in vitro according to Hyttel, J et al, *J. Neurochem*, 1985, 44, 1615; Skarsfeldt, T. et al, *Eur. J. Pharmacol.* 1986, 125, 323. Additionally some of the compounds of the invention were tested with respect to dopamine $D_2$ receptor binding activity according to van der Welde et al, *Eur. J. Pharmacol.* 1987, 134, 211, with respect to serotonin 5-HT$_{1A}$ receptor binding activity according to Hyttel et al. *Drug Dev. Res.*, 1988. 15, 389–404, and with respect to serotonin 5-HT$_2$ receptor binding activity according to Hyttel, Pharmacology & Toxicology, 1987, 61, 126–129.

For most compounds, the affinities for $\alpha_1$ adrenoceptors and $D_2$, 5-HT$_{1A}$, and 5-HT$_2$ receptors were very inferior as compared to the potent binding to sigma receptors. Thus many of the compounds are very selective sigma receptor ligands. For example with respect to the $\alpha_1$ adrenoceptors and dopamine $D_2$, serotonin 5-HT$_{1A}$ and 5-HT$_2$ receptors, ratios of binding IC$_{50}$ values (alpha/sigma, dopamine/sigma, 5-HT$_{1A}$/sigma, and 5-HT$_2$/sigma, respectively) of 100→1000 have been found.

FORMULATION EXAMPLES

The pharmaceutical formulations of the invention may be prepared by conventional methods in the art. For example: Tablets may be prepared by mixing the active ingredient with ordinary adjuvants and/or diluents and subsequently compressing the mixture in a conventional tabletting maschine. Examples of adjuvants or diluents comprise: corn starch, lactose, talcum, magnesium stearate, gelatine, lactose, gums, etc. Other adjuvants or additives usually used for such purposes such as colourings, flavourings, preservatives etc. may be used provided that they are compatible with the active ingredients. Solutions for injections may be prepared by dissolving the active ingredient and possible additives in a part of the vehicle, preferably sterile water, adjusting the solution to desired volume, sterilization of the solution and filling in suitable ampules or vials. Any suitable additive conventionally used in the art may be added, e.g. tonicity agents, preservatives, antioxidants, etc.

Typical examples of recipes for the formulation of the invention are as follows:

1) Tablets containing 5.0 mg of Compound 1b calculated as the free base:

Comp. 1b 5.0 mg

Lactose 60 mg

Maize Starch 30 mg

Hydroxypropylcellulose 2.4 mg

Microcrystalline Cellulose 19.2 mg

Croscarmellose Sodium Type A 2.4 mg

Magnesium Stearate 0.84 mg

2) Tablets containing 1.0 mg of Compound 1e calculated as the free base:

Comp. 1e 1.0 mg

Lactose 23.5 mg

Maize Starch 46.9 mg

Povidone 1.8 mg

Microcrystalline Cellulose 14.4 mg

Croscarmellose Sodium Type A 1.8 mg

Magnesium stearate 0.63 mg

3) Syrup containing per milliliter:

Comp. 1s 2.5 mg

Sorbitol 500 mg

Hydroxyethylcellulose 15 mg

Glycerol 50 mg

Methyl-paraben 1 mg

Propyl-paraben 0.1 mg

Ethanol 0.005 ml

Flavour 0.05 mg

Saccharin Natrium 0.5 mg

Water ad 1 ml

4) Solution for injection containing per milliliter:

Comp. 2b 0.5 mg

Sorbitol 5.1 mg

Acetic acid, Glacial 0.08 mg

Water for injection ad 1 ml.

We claim:

1. A dimeric 4-phenylpiperidine, 4-phenyl-1,2,3,6-tetrahydropyridine compound or a dimeric spirocyclic piperidine compound having the formula:

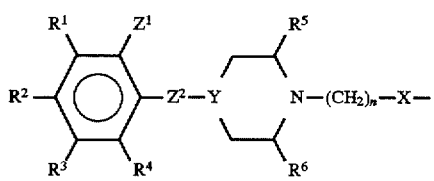

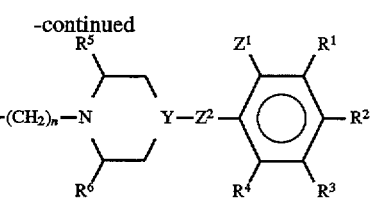

wherein n is 1–5;

$R^1$ to $R^4$ are independently selected from hydrogen, halogen, $C_{1-6}$ alkyl, $C_{1-6}$ alkoxy, hydroxy, $C_{1-6}$ alkylthio, $C_{1-6}$ alkylsufonyl, $C_{1-6}$ alkyl- or di-$C_{1-6}$ alkyl)amino, cyano, trifluoromethyl, nitro, trifluoromethylthio or trifluoromethylsulfonyloxy;

$R^5$ and $R^6$ are $C_{2-3}$ alkyl linked together forming an ethylene or propylene bridge;

X is O, S, SO, $SO_2$, CO or $(CH_2)_m$, m being 0 or 1, X is $NR^7$, $R^7$ being H, $C_{1-6}$ alkyl, cycloalkyl, cycloalkylalkyl, phenyl or phenylalkyl, or X is $CR^8R^9$, wherein $R^8$ and $R^9$ are independently selected from the group consisting of hydroxy and the substituents defined under $R^7$, any phenyl group being optionally substituted with one or more substituents selected from the group consisting of halogen, $C_{1-6}$ alkyl, $C_{1-6}$ alkoxy, hydroxy, $C_{1-6}$ alkylthio, $C_{1-6}$ alkylsulfonyl, $C_{1-6}$ alkyl or di($C_{1-6}$ alkyl)amino, cyano, trifluoromethyl and trifluoromethylthio; and $Z^1$ and Y are linked together via a single bond, thereby forming a spirocyclic junction; wherein Y is C;

$Z^1$ is O, S, $(CH_2)_q$, q being 1, 2 or 3, or $Z^1$ is $CH_2O$, $CH_2S$, $CH_2CH_2O$, $CH_2CH_2S$, CH=CH, CH=CHCH$_2$, $CH_2OCH_2$, $CH_2SCH_2$, CH=CH—O, or CH=CH—S; and $Z^2$ is O, S, a bond or $CH_2$ with the proviso that $Z^1$ may not be O, S or $(CH_2)_q$, wherein q is 1 when $Z^2$ is a bond;

or an acid addition salt thereof.

2. A compound according to claim 1, wherein n is 1, 2 or 3.

3. A compound according to claim 1, wherein X is $(CH_2)_m$, m being 0 or 1, X is $NR^7$, $R^7$ being C1-6 alkyl, cycloalkyl, phenyl, or phenyl substituted with halogen or X is S, O or $CR^8R^9$, wherein $R^8$ is hydroxy, phenyl and or phenyl substituted with halogen and $R^9$ is hydrogen.

4. A compound according to claim 1, wherein $R^2$–$R^4$ are independently selected from the group consisting of hydrogen, halogen, $C_{1-6}$ alkyl, and trifluoromethyl.

5. A compound according to claim 1, wherein $Z^1$ is $(CH_2)_q$, q being 1, 2 or 3, or $Z^1$ is $CH_2O$, $(CH_2)_2O$, CH=CH, O, S or $CH_2S$; and $Z^2$ is O or $(CH_2)_p$ wherein p is 0 or 1.

6. A compound according to claim 5, wherein $Z^2$ is $(CH_2)_p$, p being 0, and $Z^1$ is $CH_2O$, $CH_2S$ or $(CH_2)_2O$.

7. A pharmaceutical composition comprising at least one dimeric piperidine or 1,2,3,6-tetrahydropyridine compound according to claim 1 or a pharmaceutically acceptable acid addition salt thereof in combination with one or more pharmaceutically acceptable carriers or diluents.

8. The composition according to claim 7 in unit dosage form containing said compound in an mount of 0.01 to 50 mg.

9. A method for treating anxiety, psychosis, epilepsy, convulsions, amnesia, or Parkinson's disease comprising administering a therapeutically effective amount of a compound according to claim 1 or a pharmaceutically acceptable acid addition salt thereof to a patient in need thereof.

10. A method of modulating sigma receptor activity so as to reduce anxiety in a subject comprising administering to the subject a pharmaceutically effective amount of the composition of claim 1 or a pharmaceutically acceptable addition salt thereof and a pharmaceutically acceptable carrier.

11. A method of modulating sigma receptor activity so as to reverse amnesia in a subject comprising administering to the subject a pharmaceutically effective amount of the composition of claim 1 or a pharmaceutically acceptable addition salt thereof and a pharmaceutically acceptable carrier.

12. A method of modulating sigma receptor activity so as to aleviate psychosis in a subject comprising administering to the subject a pharmaceutically effective amount of the composition of claim 1 or a pharmaceutically acceptable addition salt thereof and a pharmaceutically acceptable carrier.

13. A method of modulating sigma receptor activity so as to aleviate Parkinson's disease in a subject comprising administering to the subject a pharmaceutically effective amount of the composition of claim 1 or a pharmaceutically acceptable addition salt thereof and a pharmaceutically acceptable carrier.

14. A method of modulating sigma receptor activity so as to diminish convulsions in a subject comprising administering to the subject a pharmaceutically effective amount of the composition of claim 1 or a pharmaceutically acceptable addition salt thereof and a pharmaceutically acceptable carrier and a pharmaceutically acceptable carrier.

* * * * *